(12) United States Patent
Goldmeier

(10) Patent No.: US 10,973,943 B2
(45) Date of Patent: Apr. 13, 2021

(54) SCENTED NIGHT LIGHT

(71) Applicant: Steven Goldmeier, Plainview, NY (US)

(72) Inventor: Steven Goldmeier, Plainview, NY (US)

( * ) Notice: Subject to any disclaimer, the term of this patent is extended or adjusted under 35 U.S.C. 154(b) by 0 days.

(21) Appl. No.: 16/819,157

(22) Filed: Mar. 15, 2020

(65) Prior Publication Data
US 2020/0316243 A1 Oct. 8, 2020

Related U.S. Application Data

(63) Continuation-in-part of application No. 29/674,915, filed on Dec. 27, 2018, now Pat. No. Des. 880,023.

(51) Int. Cl.
*A61L 9/12* (2006.01)
*F21S 8/00* (2006.01)
*F21Y 115/10* (2016.01)

(52) U.S. Cl.
CPC ............... *A61L 9/125* (2013.01); *F21S 8/035* (2013.01); *F21Y 2115/10* (2016.08)

(58) Field of Classification Search
None
See application file for complete search history.

(56) References Cited

U.S. PATENT DOCUMENTS 4,714,984 A * 12/1987 Spector ................... F21S 8/035
362/101

\* cited by examiner

*Primary Examiner* — Vip Patel
(74) *Attorney, Agent, or Firm* — Alfred M. Walker

(57) ABSTRACT

A scented plug-in night light provides a pedestal for variable, interchangeable thematic character statuettes, which are illuminated by the scented plug-in night light. The scented plug-in night light is optionally provided with a digital clock incorporated into the housing for the scented night light to turn on the night at specified times to illuminate a child's favorite thematic character, which can serve as an inducement for a child who is reluctant to observe bedtime. Thereafter the illuminated thematic character of the night light stays on to act as a safety night light during the selected duration of time, and an alarm for waking the child.

17 Claims, 6 Drawing Sheets

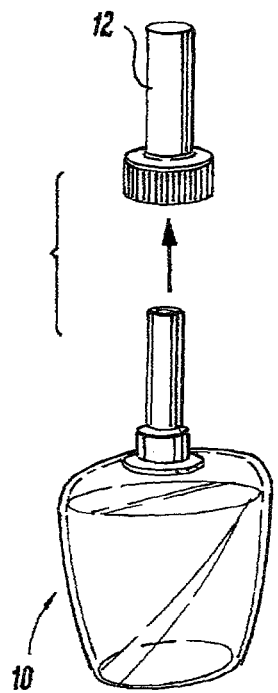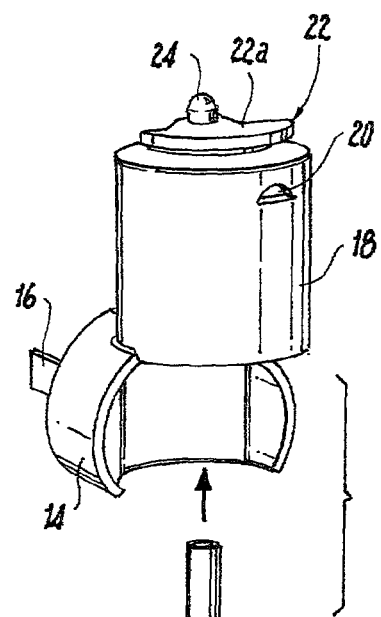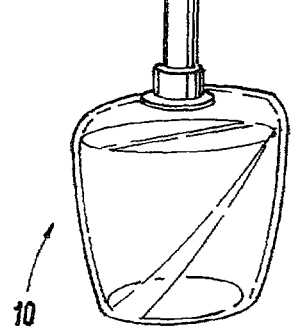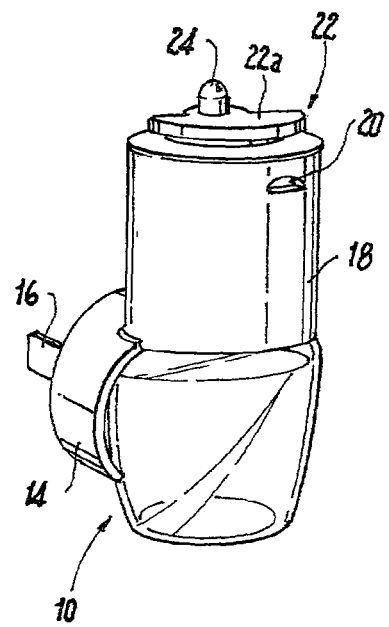
Fig. 1
Fig. 2
Fig. 3

SCENTED NIGHT LIGHT

RELATED APPLICATIONS

This application is a continuation-in-part of application Ser. No. 29/674,915, filed on Dec. 27, 2018, and claims priority in part therefrom under 35 U.S.C. § 120. The '915 application is incorporated by reference herein.

FIELD OF THE INVENTION

The present invention relates to scented, plug-in night lights which act as pedestals for variable, interchangeable thematic characters.

COPYRIGHT NOTICE

The drawings herein show an example of a statuette of a thematic character, which is supported by the housing of the scented night light described herein. The thematic character shown in drawing FIGS. 1-6 is an illustrative example only.

BACKGROUND OF THE INVENTION

Plug-in scent emitters are known commercially as well as in the prior art. U.S. Pat. No. 9,770,524 of Belongia for a volatile material dispenser relates to such a scent emitter using refills of volatile liquids which are then electrically heated in a housing. U.S. Pat. No. 5,556,192 of Wang describes a perfumer structure with an optically controlled night lamp.

OBJECTS OF THE INVENTION

It is therefore an object of the present invention to provide a scented, plug-in night light which acts as a pedestal for variable, interchangeable thematic character statuettes.

It is also an object of the present invention to provide a scented plug-in night light with an optional digital clock incorporated into the housing for the scented night light to turn on the scented night light at specified times.

It is also an object of the present invention to be used to turn on the night light at a specified time and illuminate a child's favorite thematic character, which can serve as an inducement for a child who is reluctant to observe bedtime.

Other objects which become apparent from the following description of the present invention.

SUMMARY OF THE INVENTION

The present invention combines elements of the prior art with a translucent statuette of a thematic character that is lighted by a light emitting diode (LED) and serves the function of a night light illuminating the vicinity. A variety of characters from the same theme can be adapted to snap into place.

In an alternate embodiment, an optional digital clock can be incorporated into the housing. It can be used to turn on the night light at a specified time; this might serve as an inducement for a child who is reluctant to observe bedtime (if their favorite character is also calling bedtime). Thereafter the night light stays on to act as a safety night light during the selected duration of time.

Either of the two embodiments has a manual switch which controls an internal heater whereby the unit can be plugged in while not emitting scent if desired.

BRIEF DESCRIPTION OF THE DRAWINGS

The present invention can best be understood in connection with the accompanying drawings. It is noted that the invention is not limited to the precise embodiments shown in the following drawings, in which:

FIG. 1 is a perspective view of a scent refill bottle/dispensing cartridge;

FIG. 2 is a perspective view of a refill bottle/dispensing cartridge of FIG. 1 poised to be inserted in the dispensing housing of the scented night light;

FIG. 3 is a perspective view of the scented night light housing with a refill bottle/dispensing cartridge attached;

DETAILED DESCRIPTION OF THE INVENTION

For illustrative purposes only, a preferred mode for carrying out the invention is described herein.

Figure 4:
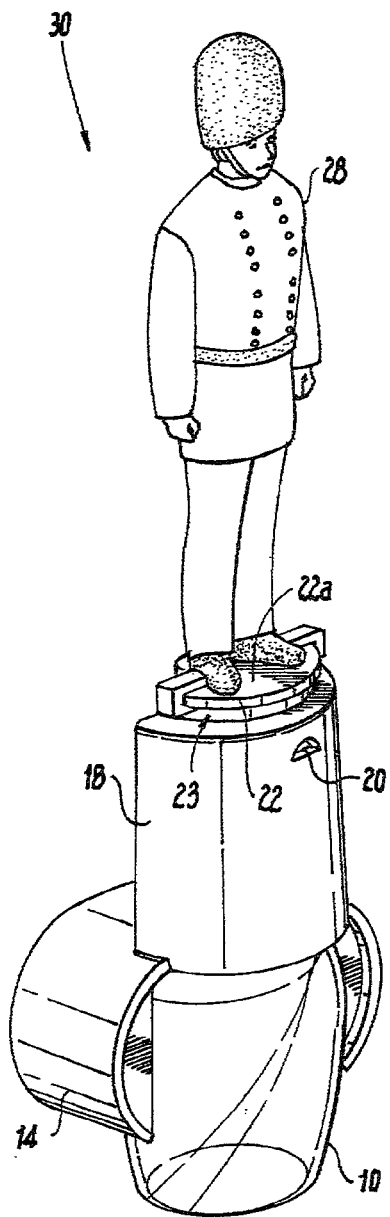
FIG. 4 is a perspective view of the scented night light with a thematic character attached; wherein for illustrative example purposes, the thematic character shown is a toy soldier.
Figure 5:
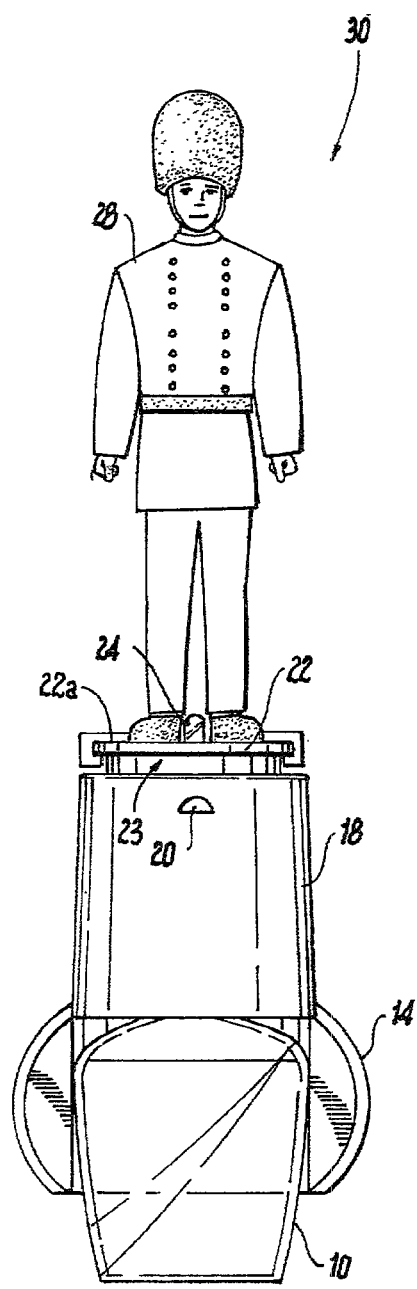
FIG. 5 is a front elevation view thereof.
Figure 6:
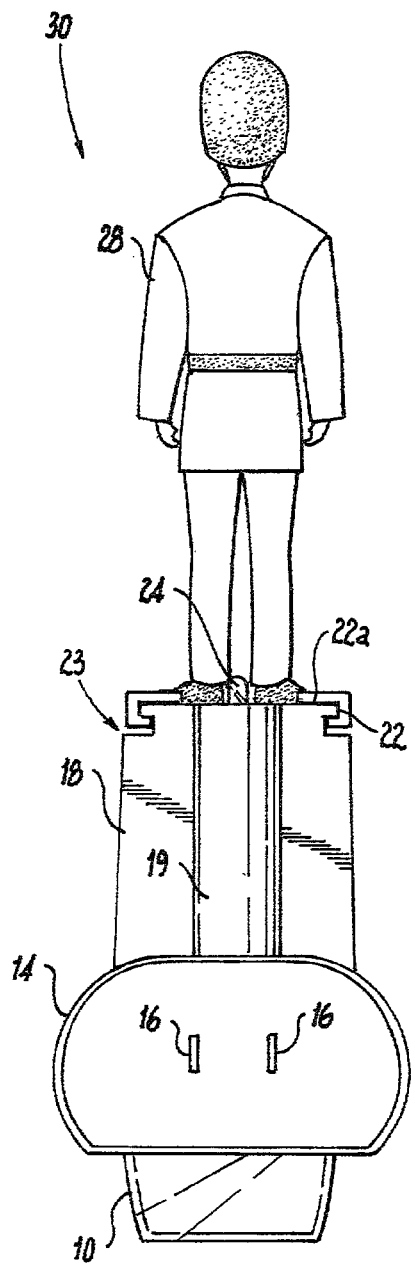
FIG. 6 is a rear elevation view thereof.
Figure 7:
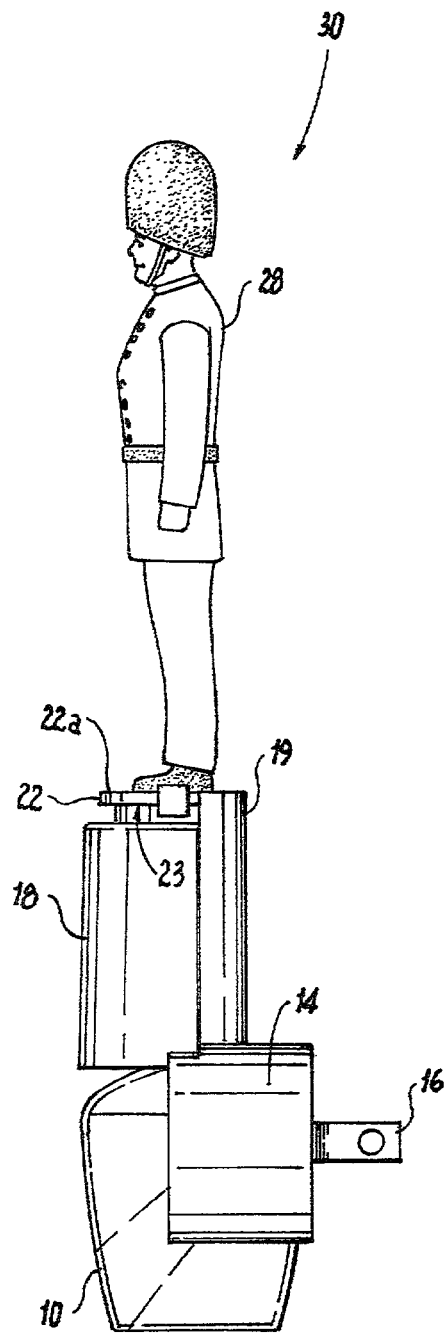
FIG. 7 is a right side elevation view thereof.
Figure 8:
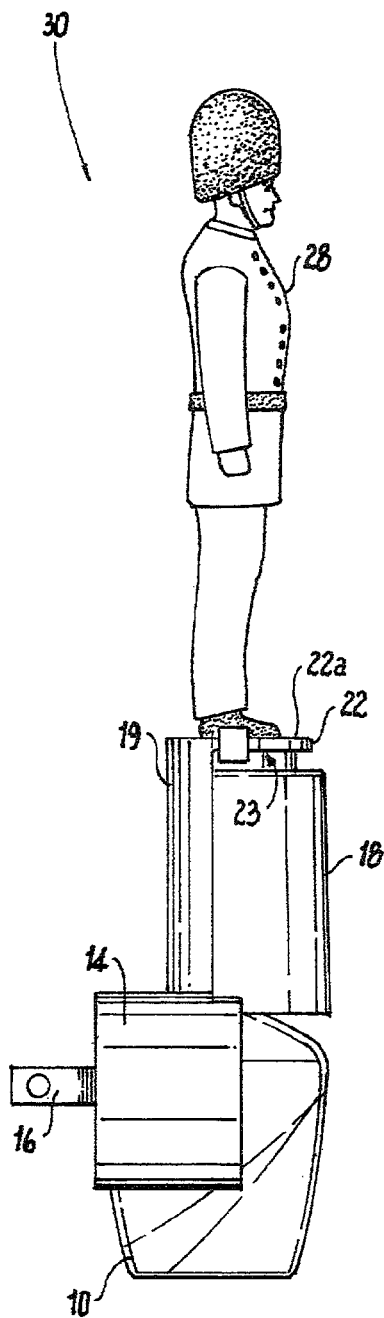
FIG. 8 is a left side elevation view thereof.
Figure 9:
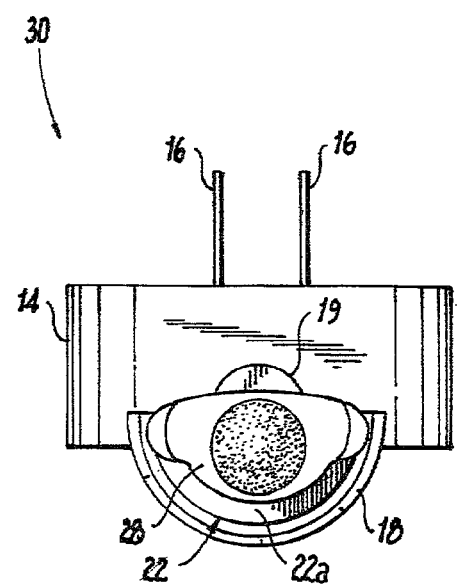
FIG. 9 is a top planar view thereof.
Figure 10:
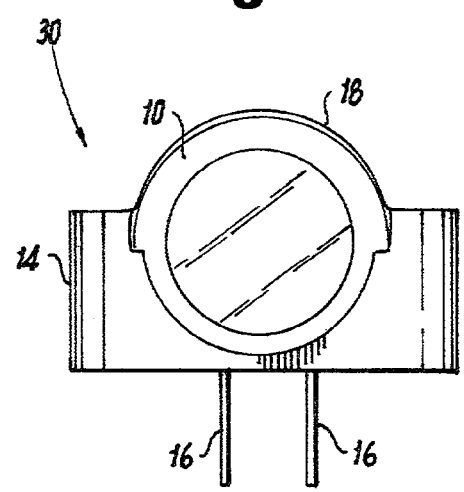
FIG. 10 is a bottom view thereof.

FIG. 1 shows a scented night light 30 with a liquid scent refill 10 having a removable cover 12, which must be removed before use. FIG. 2 shows refill 10 ready to be pushed up into lower housing 14 where it will be latched in place. One of two plug contacts 16 can be seen at the back. Upper housing 18 contains the conduit 19 to the outside vent 20 as well as the heating element. LED 24 is on the top planar surface 22a atop pedestal 22 having a groove 23 which retains the removably attachable translucent thematic FIGS. 28. Although groove 23 is shown as the means for attaching the translucent thematic character 28 on top of the upper housing 18, other means for attachment known to those skilled in the art, such as magnets or hook and loop fasteners (i.e., VELCRO®) may be employed. FIGS. 4 and 5 show the assembled scented night light 30 with the aforementioned attached translucent thematic character FIG. 28. Applicant notes that this character is an illustrative example only, which may be one of a set of a plurality of related thematic characters.

Figure 11:
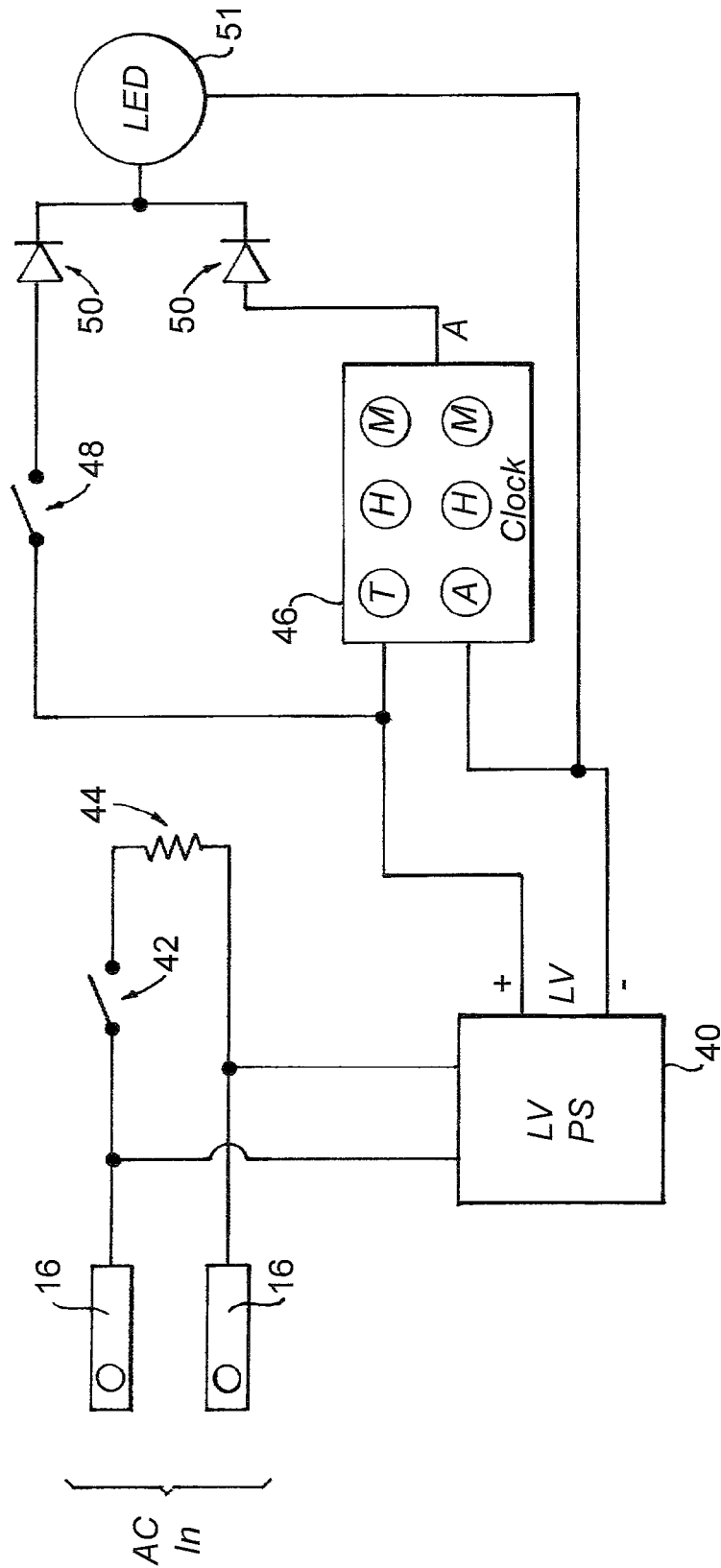
FIG. 11 is a schematic diagram of the device.

FIG. 11 is a schematic diagram including the digital clock of the second embodiment. The high voltage AC enters via wall prong plug contacts 16. Heating resistor 44 is controlled by manual switch 42. By eliminating switch 42, the scent feature will be on whenever the unit is plugged in. Switch 42 permits one to keep the unit plugged in while in an OFF mode. A rudimentary low voltage power supply 40 supplies a nominal low voltage DC as required by the LED and the digital clock module 46 (if used). Clock 46 is a non-typical solid-state module with means for setting time of day as well as alarm time. In this case, the output line marked A turns continuously live when the alarm button is pressed. At the time set for the alarm (there is no audible alarm) line A is turned off. If switch 48 were open, clock 46 would control and turn on the night light LED 51 through isolation diode 50. Thereafter the night light LED 51 stays on to act as a safety night light during the selected duration of time. Clock 46 would turn off the voltage at A after a fixed time (for example, 10 hours).

Clock 46 can disable the alarm. With "alarm" disabled, switch 48 can manually control LED 51 through an isolation diode 50.

Figure 12:
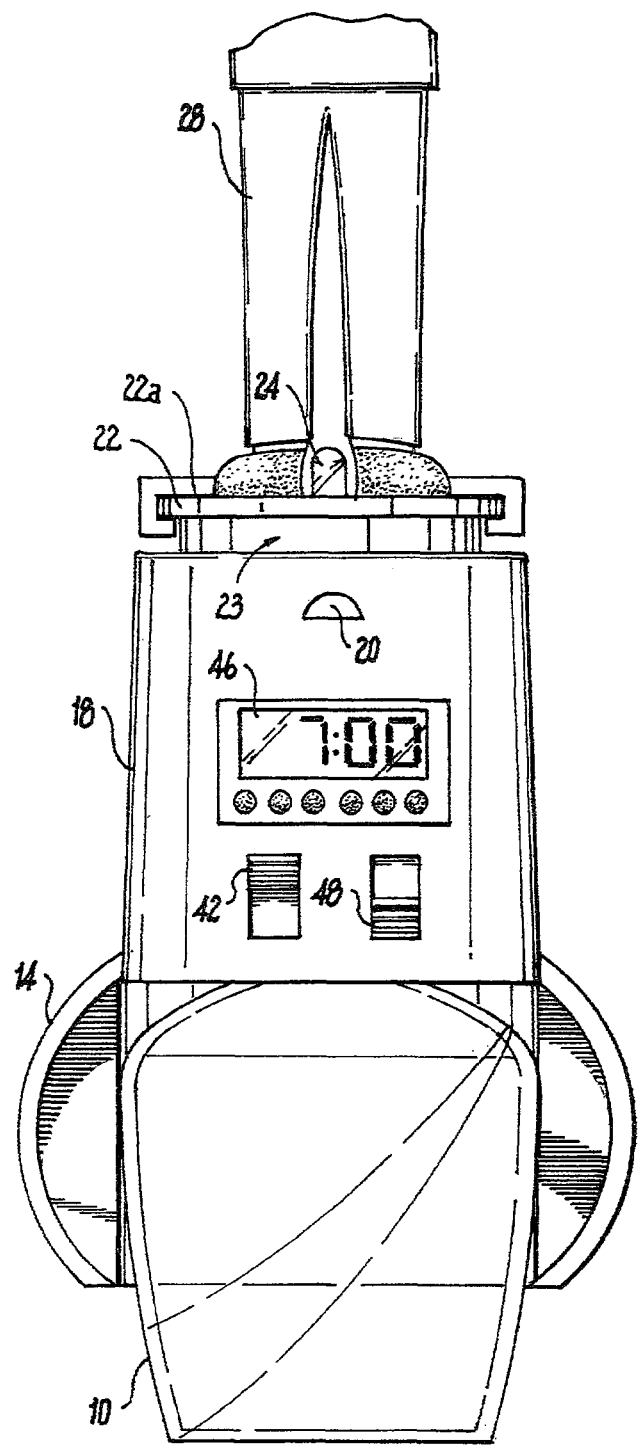
FIG. 12 is a front elevation of a detail of the scented night light with the digital clock feature.

FIG. 12 is a detail view of the scented night light 30 showing the digital clock 46 and switches 42 and 48 for activation of the scent emitter 10 or the digital clock 46.

The clock feature can be eliminated completely by leaving out clock module 46 and blocking diodes 50 from the schematic diagram. It is noted that one can also substitute an optically sensitive switch for switch 48 as in the prior art to operate the night light function by ambient light level.

In an alternate embodiment, clock 46 would retain an audio alarm element in the form of a short digital message (any stored sound bytes such as voice or music) to be played at alarm time simultaneously with turning LED 51 off. (This technology is readily available as illustrated by musical or talking greeting cards.) For example, the voice of a familiar cartoon character with musical background could help a child to welcome a new day.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention.

I claim:

1. A scented plug-in night light comprising:
   a light source,
   an upper housing having a support supporting a refillable scent emitter extending therein,
   a lower housing having a plug-in night light and a fastener supporting said refillable scent emitter in said upper housing,
   a pedestal on said upper housing having an upper support member supporting a variable, interchangeable translucent thematic character statuette removably attachable thereon for emitting light therethrough,
   said variable, interchangeable translucent thematic character statuette illuminated by said scented, plug-in night light.

2. The scented plug-in night light as in claim 1 further comprising a digital clock incorporated into the upper housing for the scented night light to turn on the night light at specified times to illuminate said translucent thematic character statuette, said translucent thematic character statuette being a child's favorite thematic character, which can serve as an inducement for a child who is reluctant to observe bedtime.

3. The scented plug-in night light as in claim 1 further comprising a liquid scent refill with a removable cover which must be removed before use.

4. The scented plug-in night light as in claim 3 wherein said refill is pushed up and latched into said lower housing.

5. The scented plug-in night light as in claim 4 further comprising said lower housing having a light, a power source and electrical plug contacts insertable into an AC power plug socket.

6. The scented plug-in night light as in claim 2 further comprising said upper housing containing a conduit to an outside vent and a heating element, and a light is on the top planar surface of said upper housing atop a groove which retains the translucent thematic character statuette upon said pedestal of said upper housing.

7. The scented plug-in night light is in claim 1 wherein said night light includes an LED light.

8. The scented plug-in night light as in claim 2 wherein said digital clock has a power source from high voltage AC entering via wall prong plug contacts, and a heating resistor is controlled by a manual switch, permitting the unit plugged in to be on while in an OFF mode.

9. The scented plug-in night light as in claim 6, wherein a low voltage power supply supplies a nominal low voltage DC to power the light and the digital clock module, wherein said clock is a non-typical solid-state module with a means for setting time of day as well as alarm time.

10. The scented plug-in night light as in claim 9 wherein a further switch is provided to turn on said night light through an isolation diode, said switch turning off the voltage of the clock after a fixed time.

11. The scented plug-in night light as in claim 9 further comprising a manual switch for disablement of said alarm.

12. The scented plug-in night light as in claim 9 further comprising an optically sensitive switch to operate said scented night light by ambient light level.

13. The scented plug-in night light as in claim 2 further comprising said clock retaining an audio alarm element in the form of a short digital message to be played at a designated alarm time.

14. The scented plug-in night light as in claim 13 wherein said designated alarm time is simultaneous with turning off of an LED light.

15. The scented plug-in night light as in claim 13 wherein said audio alarm is at least one stored sound byte of a story telling voice associated with said selected translucent thematic character statuette.

16. The scented plug-in night light as in claim 13 wherein said audio alarm comprises music.

17. A scented plug-in night light comprising:
   a light source,
   an upper housing having a support supporting a refillable scent emitter and a translucent surface for emitting light therethrough,
   a lower housing having a plug-in night light,
   a pedestal on said upper housing having an upper support member supporting a variable, interchangeable translucent thematic character statuette removably attachable thereon,
   said variable, interchangeable translucent thematic character statuette illuminated by said scented, plug-in night light;
   a digital clock incorporated into the housing for the scented night light to turn on the night light at specified times to illuminate said translucent thematic character statuette, said translucent thematic character statuette being a child's favorite thematic character, which can serve as an inducement for a child who is reluctant to observe bedtime,
   a liquid scent refill with a removable cover which must be removed before use, wherein said refill is pushed up and latched into said lower housing,
   said lower housing having a light, a power source and electrical plug contacts insertable into an AC power plug socket,
   said upper housing containing a conduit to an outside vent and a heating element, and a light is on the top planar surface atop a groove which retains the translucent thematic character statuette, wherein said digital clock has a power source from high voltage AC entering via wall prong plug contacts, and a heating resistor is controlled by a manual switch, permitting the unit plugged in to be on while in an OFF mode, wherein a low voltage power supply supplies a nominal low voltage DC to power the light and the digital clock module, wherein said clock is a non-typical solid-state module with a means for setting time of day as well as alarm time, wherein a further switch is provided to turn on said night light through an isolation diode, said switch turning off the voltage of the clock after a fixed time;

an optically sensitive switch to operate said scented night light by ambient light level, said clock retaining an audio alarm element in the form of a short digital message to be played at a designated alarm time, wherein said designated alarm time is simultaneous with turning off of said light source, wherein said audio alarm is at least one of stored sound byte of a story telling voice associated with said selected translucent thematic character statuette and of music.

* * * * *